(12) United States Patent
Inoue et al.

(10) Patent No.: US 6,982,362 B1
(45) Date of Patent: Jan. 3, 2006

(54) α-TOCOPHEROL TRANSPORT PROTEIN KNOCKOUT ANIMAL

(75) Inventors: Keizo Inoue, 17-605, Kantozaimukyoku-Ecchujimajyutaku, 1-3, Ecchujima, Koto-ku, Tokyo 135-0044 (JP); Hiroyuki Arai, 5-35-8-604 Koishikawa, Bunkyo-ku, Tokyo 112-0002 (JP); Makoto Arita, Kanagawa (JP); Kou-ichi Jishage, Shizuoka (JP); Hiroshi Suzuki, Shizuoka (JP)

(73) Assignees: Keizo Inoue, Tokyo (JP); Hiroyuki Arai

( * ) Notice: Subject to any disclaimer, the term of this patent is extended or adjusted under 35 U.S.C. 154(b) by 0 days.

(21) Appl. No.: 10/069,251

(22) PCT Filed: Aug. 24, 2000

(86) PCT No.: PCT/JP00/05686

§ 371 (c)(1),
(2), (4) Date: Jun. 6, 2002

(87) PCT Pub. No.: WO01/13716

PCT Pub. Date: Mar. 1, 2001

(30) Foreign Application Priority Data

Aug. 24, 1999 (JP) ................................. 11/237003

(51) Int. Cl.
*A01K 67/027* (2006.01)
*C12N 15/00* (2006.01)

(52) U.S. Cl. .......................................... 800/18; 800/21
(58) Field of Classification Search .................. 800/14, 800/18, 21, 15, 16, 17, 3
See application file for complete search history.

(56) References Cited

OTHER PUBLICATIONS

Leonard, 1995, Immunological Reviews, vol. 148, pp. 98-113.*
Moens, 1993, Development, vol. 119, pp. 485-499.*
Griffiths, 1998, Microscopy Research and Technique, vol. 41, pp. 344-358.*
Hammer, 1990, Cell, vol. 63, 1099-1112).*
Mullins, 1990, Nature, vol. 344, 541-544.*
Mullins, 1989, EMBO J., vol. 8, pp. 4065-4072.*
Taurog, 1988, Jour. Immunol., vol. 141, pp. 4020-4023.*
Wall, 1996, Theriogenology, vol. 45, pp. 57-68.*
Overbeek, 1994, "Factors affecting transgenic animal production," Transgenic animal technology, pp. 96-98.*
Mullins, 1996, J. Clin. Invest., vol. 98, pp. S37-S40.*
Arai, 1998, FASEB Journal, vol. 12 pp. A658).*
Capecchi, 1994, Scientific American, Mar. 1994, pp. 52-59.*
Campbell and Wilmut , 1997, Theriogenology, vol. 47, pp, 63-72.*
Robins, 1981, Cell, vol. 23, pp. 29-39.*
Cavalier, 1998, Am J Hum Genet, vol. 62, p. 301-310.*
Thomas, 1993, J Anat, vol. 183, pp. 451-461.*
http://www.dddmag.com/Glossary.aspx?RPTID=KWSRCH&SEARCHMETHOD=WORD&SEARCHWORD=Knockout.*
Jones, Jeffrey M. et al., "Human Embryonic Stem Cell Technology," Seminars in *Reproductive Medicine*, vol. 18, No. 2, pp. 219-223 (2000).
Ledermann, B., "Special Review Series—Gene Manipulation and Integrative Physiology, Embryonic Stem Cells and Gene Targeting," *Experimental Physiology*, vol. 85, No. 6, pp. 603-613 (2000).
Prelle, Katja et al., "Establishment of Pluripotent Cell Lines from Vertebrate Species—Present Status and Future Prospects," *Cells Tissues Organs*, vol. 165, pp. 220-236 (1999).
"Embryonic Stem Cell Research—Still at the Starting Gate," *The Lancet* (*Oncology*), p. 523 (2001).
Sato, Y. et al., "Primary Structure of α-Tocopherol Transfer Protein From Rat Liver: Homology with Cellular Retinaldehyde-Binding Protein", The Journal of Biological Chemistry, vol. 268, No. 24, pp. 17705-17710, (1993).
Arita, M. et al., "Human α-Tocopherol Transfer Protein: cDNA Cloning, Expression and Chromosomal Localization", Biochemistry Journal, vol. 306, No. 2, pp. 437-443, (1995).
Ouahchi, K. et al., "Ataxia with Isolated Vitamin E Deficiency is Caused by Mutations in the α-Tocopherol Transfer Protein", Nature Genetics, vol. 9, No. 2, pp. 141-145, (1995).
Mansour, S.L. et al., "Disruption of the Proto-Oncogene int-2 in Mouse Embryo-Derived Stem Cells: a General Strategy for Targeting Mutations to Non-Selectable Genes", Nature, vol. 336, No. 24, pp. 348-352, (1998).
Abstracts From the 72nd Scientific Sessions, Circulation, vol. 100, No. 18, Supp.[S], pp. 231, (Nov. 2, 1999).
Arita, Makoto et al., "α-Tocopherol Transfer Protein Stimulates the Secretion of α-Tocopherol from a Cultural Liver Cell line Through a Brefeldin A-insensitive Pathway," *Proc. Natl. Acad. Sci. USA*, vol. 94, pp. 12437-12441 (1997).
Rudmann, Daniel G. et al., "Utilization of Genetically Altered Animals in the Pharmaceutical Industry," *Toxicologic Pathology*, vol. 27, No. 1, pp. 111-114 (1999).
Traber, Maret G. et al., "Molecular Mechanisms of Vitamin E Transport," *Annu. Rev. Nutr.*, vol. 19, pp. 343-355 (1999).
Copy of European Search Report, dated Oct. 13, 2004.

* cited by examiner

*Primary Examiner*—Joseph Woitach
*Assistant Examiner*—Valarie Bertoglio
(74) *Attorney, Agent, or Firm*—Finnegan, Henderson, Farabow, Garrett & Dunner, L.L.P.

(57) ABSTRACT

The present invention provides a knockout animal artificially modified to inhibit α-TTP gene expression. This animal is useful as a tool for understanding mechanisms for the development of familial isolated vitamin E deficiency and other diseases induced by oxidative stress (e.g., arteriosclerosis, diabetes). It is also useful as a tool for developing a therapeutic agent for these diseases.

7 Claims, 5 Drawing Sheets

α-TOCOPHEROL TRANSPORT PROTEIN KNOCKOUT ANIMAL

The present invention relates to a mammal modified to inhibit the expression of its gene for α-tocopherol transfer protein (hereinafter, referred to as "(α-TTP"). Human α-TTP gene is a causative gene for familial isolated vitamin E deficiency. The mammal can therefore be used for the development of a therapeutic method and/or agent for the disease, as well as for the development of a therapeutic method and/or agent for oxidative stress-induced diseases such as arteriosclerosis or diabetes.

BACKGROUND OF THE INVENTION

Oxygen is essential for living organisms, but it also has a dangerous aspect of causing unwanted oxidation of organisms' components. Living organisms have a series of defense mechanisms against such an oxidative stress. Vitamin E is one of important anti-oxidative substances in the living organisms. Among organism's components, a biomembrane phospholipid (particularly, a polyunsaturated fatty acid chain in phospholipid) is most likely to receive an attack by oxygen. When biomembranes undergo an oxidative impairment, the membrane permeability increases, and finally leading to cell death. Vitamin E is lipid-soluble (lipophilic) and usually buried in biomembrane bilayers in cells. It plays the most dominant role in preventing biomembrane oxidation.

As a protein cable of specifically binding to this vitamin E, α-TTP was isolated from a soluble fraction of rat liver and found to enhance intermembrane transfer (Eur. J. Biochem. 177, 537, 1981). In addition, purification and gene structure analysis were also performed on this protein (J. Biol. Chem. 268, 17705, 1993; Biochem. J. 306, 437, 1995). Further, human α-TTP gene was shown to be a causative gene per se for a hereditary disease called "familial isolated vitamin E deficiency (FIVE deficiency)" (Nature Genetics 9, 141, 1995).

Familial isolated vitamin E deficiency has previously been known as a hereditary disease which produces no increase in vitamin E level in the body, even when much vitamin E is taken into the body. A patient with this disease suffers from necrosis of nerves, particularly sensory nerves, and in a serious case he will die around 20 years of age. Vitamin E circulates in the blood as a conjugate with plasma lipoprotein and then enters peripheral tissues. Meanwhile, plasma lipoprotein is secreted from the liver and finally returns to the liver to be metabolized. Vitamin E absorbed from food through blood vessels is incorporated onto lipoprotein (VLDL) in the liver. In this hereditary disease, an impairment is found in just this process, i.e., an incorporation process of vitamin E onto VLDL in the liver.

In view of these circumstances, the object of the present invention is to provide a non-human mammal useful in analyzing α-TTP functions and developing a therapeutic agent for diseases caused by α-TTP mutation. In the prior art, an animal could enter a vitamin E deficient state by feeding it with a vitamin E-deficient diet, but in a normal animal, a very long period of time was required to achieve complete clearance of vitamin E from the animal body because the normal animal has an efficient re-circulation system for vitamin E (this system involves α-TTP). In the present invention, an animal with a disrupted α-TTP gene involved in this vitamin E re-circulation system is created to provide a congenitally vitamin E-deficient animal model highly sensitive to oxidative stress, which is advantageous in understanding diseases caused by vitamin E deficiency, i.e., deficiency of anti-oxidative substances critical for the body, and in developing a therapeutic agent for such diseases. More specifically, the object of the present invention is to provide a knockout animal artificially modified to inhibit α-TTP gene expression and a method for producing the animal.

BRIEF DESCRIPTION OF THE DRAWINGS

FIG. 4-1 shows the electrophoresis results of mouse genomic DNA fragments.

FIG. 4-2 shows the results of Southern hybridization using a probe having a sequence around Exon 1.

FIG. 5-1 shows the results of Northern hybridization using mouse α-TTP cDNA as a probe.

FIG. 5-2 shows the intensity of signals from Northern hybridization.

SUMMARY OF THE INVENTION

Figure 1:
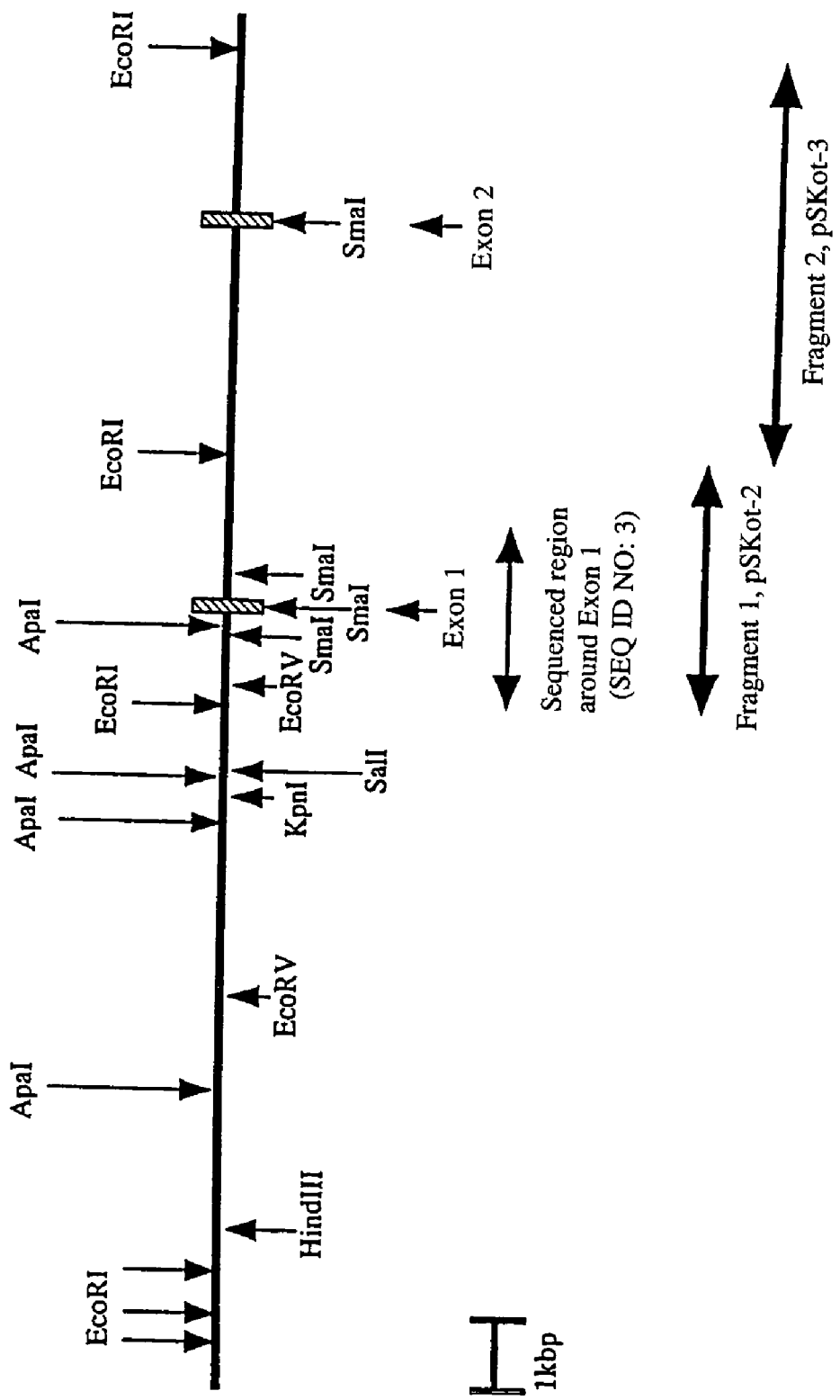
FIG. 1 shows a restriction site map of BS-MG6.

We tried to generate a mammal model with an artificially disrupted α-TTP gene. Specifically, as shown in the Examples in more detail, mouse α-TTP gene (cDNA, genomic DNA) was cloned and used to construct a vector for homologous recombination, which was then introduced into mouse embryonic stem cells (ES cells) to obtain a recombinant clone. The recombinant clone was then transferred to a recipient mouse, thereby successfully obtaining a mouse with a mutated α-TTP gene. Mammals obtained according to the present invention or established cell lines prepared therefrom are considered to be useful tools for understanding mechanisms for the development of various diseases caused by a disrupted α-TTP gene and other disease conditions suspected to be associated with oxidative stress (e.g., arteriosclerosis, diabetes, ischemic diseases, Parkinson's disease) and further considered to be very useful tools for developing a therapeutic method and/or agent for these diseases. They are therefore expected to be used for a variety of purposes.

The present invention relates to the following embodiments (1) to (4):

(1) a non-human mammal artificially modified to inhibit the expression of its endogenous gene encoding α-TTP, and a non-human mammal cell prepared therefrom;

(2) a non-human mammal cell artificially modified to inhibit the expression of its endogenous gene encoding α-TTP, said cell having the ability to differentiate into an individual;

(3) a method for producing the non-human mammal of (1) above, which comprises the steps of: (a) inserting the non-human mammal cell of (2) above into an embryo taken from a pregnant female, and (b) transferring the embryo into the uterus of a pseudopregnant female; and (4) a method for screening medicaments, which comprises using the non-human mammal of (1) above or the non-human mammal cell of (1) or (2) above, and a medicament obtained thereby.

DETAILED DESCRIPTION OF THE INVENTION

The present invention will be described below in more detail.

(1) Knockout Animals and Cells Prepared Therefrom

The knockout animal and cells prepared therefrom of the present invention are characterized by being artificially modified to inhibit the expression of their endogenous gene encoding α-TTP.

Examples of a means for modifying an animal or cell to inhibit gene expression include, but are not limited to, a means for disrupting a part of the α-TTP gene or an expression regulatory region thereof. As used herein, the phrase "inhibit gene expression" or "inhibit the expression" encompasses both complete and partial inhibition. It also encompasses inhibition caused in a particular environment. Further, it encompasses a case where one of two alleles is inhibited from expressing.

Any type of animal may be used, so long as it is a mammal other than human. Preferred animals are those belonging to Rodent, including mouse, rat, hamster and rabbit, with mouse being particularly preferred among these.

The knockout animal of the present invention may be prepared, for example, in the manner stated below.

The knockout animal of the present invention is useful in developing a therapeutic agent and/or method for diseases caused by impaired functions of the α-TTP gene and/or diseases induced by oxidative stress. For example, the knockout animal of the present invention is administered with a test compound to assay the compound for its effect on arteriosclerosis or diabetes, thereby selecting a compound having a desired effect. This enables the acquisition of a potential candidate for a therapeutic agent.

In addition, cells prepared from the knockout animal of the present invention are contemplated to be used for the development of a therapeutic agent and/or method for the diseases mentioned above. For example, cells are prepared from an embryo or the like of the knockout animal according to the present invention, and then contacted with a test compound to assay the compound for its effect on oxidative impairment of the cell membranes etc., thereby selecting a compound having a desired effect. Cells to be used may be either primary cultured cells or established cell lines prepared therefrom. The compound thus screened may be a potential candidate for a medicament.

(2) Animal Cells

The animal cells of the present invention are characterized by being artificially modified to inhibit the expression of their endogenous gene encoding α-TTP and by their ability to differentiate into an individual.

A means for modifying a cell to inhibit gene expression and the meaning thereof, as well as the type of animal to be used are as defined for the above knockout animal.

The animal cells of the present invention may be prepared in any manner. To prepare cells modified to inhibit α-TTP gene expression through disruption of at least a part of the α-TTP gene or an expression regulatory region thereof, a homologous recombination (knockout) vector may be constructed and introduced into appropriate cells.

The homologous recombination vector comprises a nucleotide sequence designed to inactivate an endogenous α-TTP gene of a target animal. Such a nucleotide sequence may be, for example, a nucleotide sequence lacking at least a part of the α-TTP gene or an expression regulatory region thereof or a nucleotide sequence containing another gene inserted into the sequence of the α-TTP gene or an expression regulatory region thereof. Preferably, another gene thus inserted into the sequence of the α-TTP gene or an expression regulatory region thereof may also function as a marker. Examples of such a gene include a drug-resistance gene such as neomycin-resistance gene (for G418 resistance selection) and thymidine kinase gene (for ganciclovir resistance selection); a toxin gene such as diphteria toxin (DT) A gene; or combinations thereof. These genes may be inserted into any site on the α-TTP gene, so long as the inserted gene can inhibit the expression of an endogenous α-TTP gene in a target.

The insertion of these genes into the sequence of the cloned α-TTP gene may be accomplished in vitro by standard DNA recombination techniques (See, Sambrook, J. et al., Molecular Cloning, Cold Spring Harbor Laboratory Press (1989)).

The homologous recombination vector thus constructed is introduced into cells having the ability to differentiate into an individual (e.g., ES cells) to cause homologous recombination between the vector and the α-TTP gene in the cells.

The homologous recombination vector may be introduced into the cells in a manner well known to those skilled in the art, for example, by using an electroporation technique. As a result, in some of the cells, homologous recombination occurs between the cellular α-TTP gene and the corresponding region of the homologous recombination vector, thereby replacing the wild-type gene by a gene constructed in the homologous recombination vector. Thus, cells having a modified α-TTP gene containing the inserted marker gene can be obtained.

In a case where a marker gene is used in the homologous recombination vector, cells undergoing a desired homologous recombination event will have an inactivated α-TTP gene and will also attain the marker gene, thereby allowing the use of this marker gene as an indicator for cell screening. For example, when a drug resistance gene is used as a marker gene, cells which have been subjected to vector introduction may be screened for a desired homologous recombination event by culturing the cells in the presence of the drug at a lethal level.

The animal cells of the present invention may be used for production of the knockout animal stated above. These cells may also be used for screening of medicaments, as in the case of the cells prepared from the knockout animal according to the present invention.

(3) Method for Production of Non-Human Mammals

The method for producing a non-human mammal of the present invention comprises the steps of: (a) inserting the non-human mammal cell described above into an embryo taken from a pregnant female to form a chimeric embryo, and (b) transferring the chimeric embryo into the uterus of a pseudopregnant female.

(a) Step of Forming Chimeric Embryos

In a case where ES cells are used for insertion into embryos, these cells may be injected into blastocysts to form chimeric embryos. Blastocysts to be used for injection may be obtained by flushing the uteri of pregnant females.

(b) Step of Transferring Chimeric Embryos

The chimeric embryos may be transferred into the uterine horns of pseudopregnant mammals to obtain chimeric animals. In order to permit a determination in the resulting animals as to whether the injected cells (ES cells) have been successfully incorporated into developing embryos, it is desirable to choose blastocysts such that the resulting animals have a visual difference (e.g., coat color) between parts originating from the injected cells and parts originating from blastocysts.

Following the above two steps, the resulting chimeric animal is crossed with an appropriate animal line of the same species to obtain pups. If the chimeric animal has germ cells derived from the injected cells, pups modified to inhibit α-TTP gene expression can be obtained.

(4) Method for Screening Medicaments and Medicaments Obtained Thereby

The method for screening medicaments of the present invention is characterized by using the non-human mammals or non-human mammal cells mentioned above.

The non-human mammal etc. of the present invention may be a model for diseases caused by impaired functions of the α-TTP gene (e.g., familial isolated vitamin E deficiency) and diseases induced by oxidative stress (e.g., arteriosclerosis, diabetes, ischemic diseases, Parkinson's disease), and hence may be used to screen therapeutic and prophylactic agents for these diseases.

EXAMPLES

The present invention will be further described in the following examples. The examples are provided for illustrative purposes only, and are not intended to limit the scope of the invention.

Example 1

Construction of Homologous Recombination Vectors for α-TTP Gene

In this example, to construct a homologous recombination vector for mouse α-TTP gene, mouse genomic α-TTP gene was first cloned. This genomic DNA was then used to construct a homologous recombination vector carrying both a neomycin-resistance gene and a thymidine kinase gene inserted thereinto for positive/negative selection, according to the report of Mansour et al. (Nature 336, 348, 1988). The neomycin-resistance gene was inserted to replace Exon 1 of α-TTP gene such that no normal α-TTP would be produced. Details will be described below.

A. Cloning of Mouse α-TTP Gene

A C57BL/6 mouse liver cDNA library (Lambda gt22A) was prepared using a SUPERSCRIPT Lambda System (GIBCO BRL). Plaque hybridization was performed on this library using the entire open reading frame of rat TTP cDNA as a probe to obtain two positive clones, neither of which extended to the translation initiation site. In turn, RT-PCR was performed on total RNA prepared from mouse liver using MATTP-00 (AGGAATTCATGGCAGAGATGCG; SEQ ID NO: 8) and MATTP-04 (AGGGCGTAGATCTG-CACTTAAT; SEQ ID NO: 9) as primers. The sequence of MATTP-00 was obtained from a sequence of mouse genomic TTP DNA cloned separately. Sequencing for amplified products was performed to determine the entire open reading frame sequence of mouse TTP cDNA. The sequence of mouse TTP cDNA thus obtained is shown in SEQ ID NO: 1 and the amino acid sequence thereof is shown in SEQ ID NO: 2.

Mouse genomic α-TTP DNA was cloned as follows.

A 129/SVJ mouse genomic DNA Lambda FIX II library was screened by plaque hybridization using the entire open reading frame of rat TTP cDNA as a probe. Phage DNA prepared from the resulting positive clone (BS-MG6) was cleaved with a restriction enzyme EcoRI and subjected to Southern blotting by using a 5'-terminal 260 bp sequence of rat TTP as a probe to detect a fragment containing an exon with the translation initiation site, which was then subcloned into pBluescriptII (TTP-MG6).

The nucleotide sequence of TTP-MG6 (2749 bp) was sequenced to confirm that Exon 1 was present in TTP-MG6 (SEQ ID NO: 3).

The clone BS-MG6 was cleaved with major restriction enzymes (EcoRI, SmaI, KpnI, ApaI, EcoRV, SalI, HindIII) to prepare a map showing the locations of cleavage sites for these restriction enzymes (FIG. 1).

B. Construction of Homologous Recombination Vectors

The mouse α-TTP gene contained in the clone BS-MG6 phage DNA was cleaved at EcoRI sites to give two fragments (Fragments 1 and 2; FIG. 1), each of which was then subcloned into a plasmid vector. More specifically, BS-MG6 phage DNA was first cleaved with EcoRI, and the resulting fragments of approximately 3.75 kbp (Fragment 1) and of approximately 5.5 kbp (Fragment 2) were then inserted into an EcoRI site of pBluescriptII (Toyobo), which had been modified to replace a SmaI site by a SalI site via introduction of a SalI linker (Takara), to obtain clones pSKot-2 and pSKot-3, respectively.

These subclones were used to construct a homologous recombination vector as follows. First, the clone pSKot-2 was cleaved with EcoRI/EcoRV and then blunt-ended by a technique using a Takara DNA Blunting Kit (Takara) to obtain pSKot-2-1. Subsequently, pSKot-2-1 was cleaved with SmaI, into which a HindIII linker was inserted (pSKot-2-2). A neomycin-resistance gene without a polyadenylation signal was integrated into a HindIII site of pSKot-2-2 to replace Exon 1 of α-TTP by the neomycin-resistance gene (pSKot-2-2Neo). A BamHI Stop Codon linker (Nippon Gene Co., Ltd.) was then introduced into a SmaI site of Exon 2 in pSKot-3 (pSKot-3 stop codon). pSKot-2-2Neo was cleaved with EcoRI and then ligated to an EcoRI fragment cleaved from pSKot-3 stop codon (pSKot-2+3Neo). pSKot-2+3Neo was cleaved with XhoI and ligated to a thymidine kinase gene to obtain a homologous recombination vector (α-TTP Targeting Vector).

The vector thus obtained is characterized by the following features (FIG. 2):

(i) Having a neomycin-resistance gene inserted to replace Exon 1 and a stop codon sequence inserted into Exon 2;
(ii) having a thymidine kinase gene as a marker gene for negative selection; and
(iii) having regions homologous to the wild-type α-TTP gene, in which one region of approx. 0.8 kb is upstream of, and the other of approx. 8 kb is downstream of the neomycin-resistance gene.

Example 2

Establishment of Es Cells with Mutated α-TTP Gene by Homologous Recombination

In this example, a homologous recombination vector was introduced into mouse ES cells (AB2.2-Prime ES Cells; The Mouse Kit, LEXICON) by electroporation and the cells were then selectively cultured in the presence of G418. The resulting G418-resistant colonies were assayed for homologous recombination events by PCR and Southern blotting. Details will be described below.

The homologous recombination vector (α-TTP Targeting Vector) DNA (30 μg) was cleaved with NotI to give linearized DNA, which was then purified. This DNA was suspended in electroporation buffer (ESQ PBS; The Mouse Kit, LEXICON) containing $3\times10^7$ mouse ES cells (AB2.2-Prime ES Cells; The Mouse Kit, LEXICON) and subjected to gene transfer under the following conditions: a field strength of 575V/cm and a capacitance of 500 μF. Twenty-four hours after the gene transfer, the cells were selectively cultured in the presence of G418 (Genetisin, Sigma) at a final concentration of 300 μg/ml.

To culture the ES cells, a medium for ES cells (hereinafter, referred to as "ES Cell Medium") was prepared from ESQ DMEM medium (The Mouse Kit, LEXICON), which was supplemented with fetal bovine serum (ESQ FBS; The Mouse Kit, LEXICON) at a final concentration of 15%, L-glutamine (ESQ GPS; The Mouse Kit, LEXICON) at a final concentration of 2 mM, β-mercaptoethanol (ESQ BME; The Mouse Kit, LEXICON) at a final concentration of 100 μM, penicillin at a final concentration of 50 U/ml and streptomycin at a final concentration of 50 μg/ml.

In addition, ESQ Feeder cells (The Mouse Kit, LEXICON) were used as feeder cells for ES cells. To culture these feeder cells, ESQ DMEM medium supplemented with FBS at a final concentration of 7% was prepared. ESQ Feeder cells ($5\times10^7$ cells/vial) were rapidly thawed at 37° C. and then adjusted to a cell density of $4.4\times10^5$ cells/ml with the medium for feeder cells. The resulting cell suspension was aliquoted into culture devices pre-coated with gelatin (ESQ Gelatin; The Mouse Kit, LEXICON) at an amount of 12 ml for 100 mm φ dish, 4 ml for 60 mm φ dish, 2 ml/well for 6-well plate, 0.5 ml/well for 24-well plate, and 75 μl/well for 96-well plate. The feeder cells thus prepared were used within 3 weeks.

Eleven days after the gene transfer, the appearing G418-resistant colonies were subcultured to a 96-well microplate as follows. Namely, each G418-resistant colony was transferred into 30 μl of ESQ trypsin solution (The Mouse Kit, LEXICON) per well of a 96-well microplate (Corning 2586OMP) by using a micropipette, and then treated for several minutes, followed by addition of ES Cell Culture Medium (70 μl), to prepare a single cell suspension by pipetting. Each of the resulting cell suspensions was transferred to another 96-well microplate (Falcon 3072) and further cultured. After 3 days, the cells grown to confluency on the 96-well microplate were divided into two groups as follows. Namely, the cells were dispersed in 25 μl of TE, followed by addition of ES Cell Medium (25 μl), to prepare a single cell suspension by pipetting. 50 μl of 2×Freezing medium (ESQ DMEM:ESQ FBS:DMSO=2:2:1; The Mouse Kit, LEXICON) was added to the suspension, 20 μl of which was then subcultured in 150 Pμl of ES Cell Medium per well of a=gelatin-coated 96-well microplate (Iwaki 4860-020) and further cultured in order to extract DNA for use in PCR screening for homologous recombination events. The remaining ES cells were frozen and stored at −80° C. with addition of liquid paraffin (100 μl; filter-sterilized through 0.2 μm filter). The ES cells used for DNA extraction were cultured in the absence of the feeder cells, whereas all ES cells used for other purposes were cultured in the presence of the feeder cells. PCR screening for homologous recombination events was performed in the following manner. Namely, the medium was removed from each well of the 96-well plate containing the cells grown to confluency. Lysis buffer (5 μl of 10×Taq buffer, 5 μl of 5% NP-40, 4 μl of Proteinase K, 36 μl of H$_2$O) was added to each well and the plate was heated at 55° C. for 2 hours. Each lysate sample was collected in a 0.5 ml tube and treated at 95° C. for 15 minutes, followed by centrifugation at 10,000 rpm for 10 to 15 minutes. An aliquot (1 μl) of each resulting supernatant was used as template DNA for PCR.

Figure 2:
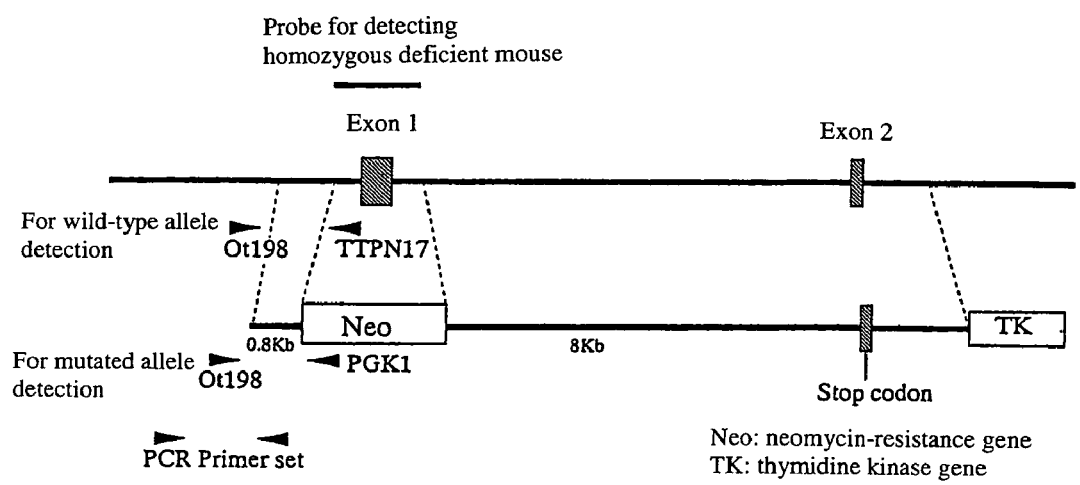
FIG. 2 shows the structure of a homologous recombination vector.

PCR primers were designed to amplify a region of approximately 0.9 kb located between PGK promoter of the neomycin-resistance gene on the homologous recombination vector and a region upstream of Exon 1 absent in the homologous recombination vector (FIG. 2).

More specifically, PCR was performed using PGK-1 primer containing a sequence on PGK promoter (5' GCTAAAGCGCATGCTCCAGACTGCCTTG 3'; SEQ ID NO: 5) and ot-198 primer located upstream of Exon 1 (5' AGCCCACACAAAAATGAAAAACGTCTCCAAG 3'; SEQ ID NO: 6) under the following conditions.

Reaction Cocktail Composition:
10×ExTaq buffer (TaKaRa) 5 μl
2.5 mM dNTPs 4 μl
ExTaq (TaKaRa) 0.5 μl
10 μM ot-198 primer 1 μl
10 μM PGK-1 primer 1 pμl
Sample 1 μl
H$_2$O 37.5 μl Reaction Conditions:
95° C. for 1 minute→(94° C. for 30 seconds→62° C. for 1 minute→72° C. for 1 minute and 20 seconds)×35 cycles→72° C. for 7 minutes Among 316 G418-resistant clones screened by PCR, 5 clones were identified as homologous recombinants (Clone L44, Clone L228, Clone L236, Clone L253 and Clone L254).

The clones, which had been confirmed to have undergone homologous recombination events by PCR screening, were subcultured to a 24-well plate from the freeze-stored 96-well plate after thawing at 37° C. This 24-well plate was cultured at 37° C. for 24 hours and the medium was then replaced to remove DMSO and liquid paraffin. When the respective clones were grown to 75 to 90% confluency, they were subcultured to a 6-well plate from the 24-well plate. When two wells in the 6-well plate showed cell growth (75 to 90% confluency), one of these two wells was provided for freeze storage and the other was provided for injection into blastocysts and DNA extraction.

Freeze storage was performed as follows. Namely, the cells were rinsed twice with ESQ PBS, and then treated with 0.5 ml of ESQ Trypsin (The Mouse Kit, LEXICON) at 37° C. for 15 to 20 minutes, followed by addition of ES Cell Medium (0.5 ml), to completely separate ES cell clusters into discrete cells by 35 to 40 pipettings. This cell suspension was transferred to a 15 ml centrifuge tube, and the well was washed again with 1 ml of ES Cell Medium, which was also collected in the tube. The tube was centrifuged at 1,000 rpm for 7 minutes to remove the medium. The cells were then re-suspended in 0.25 ml of ES Cell Medium and then mixed with 0.25 ml of 2×Freezing medium. The content of the well was transferred to a cryogenic vial, frozen at −80° C. and then stored in liquid nitrogen.

The cells to be used for injection into blastocysts and DNA extraction were prepared as follows. ES cell clusters were completely separated into discrete cells, one-fourth of which were provided for injection into blastocysts. One-third and two-thirds of the remaining cells were subcultured to 60 mm dishes coated with gelatin, respectively. In the former (one-third of the remaining cells), genomic DNA for Southern blotting was extracted from the cells grown to confluency, while in the latter (two-third of the remaining cells), the cells grown to confluency were aliquoted into 3 vials and frozen.

Example 3

Generation of Chimeric Mice from Es Cells with Recombinant α-TTP Gene

The ES cell clones, which had been confirmed to have undergone homologous recombination events, were used to form chimeric embryos by using blastocysts taken from C57BL/6J mice as host embryos. The chimeric embryos were transferred into the uterine horns of pseudopregnant mice to obtain pups. Host embryos were taken from 2-day pregnant mice by flushing their uterine tubes and uteri with Whitten's medium supplemented with 100 μM EDTA. Eight-celled embryos or morulas were cultured in Whitten's medium for 24 hours and the resulting blastocysts were provided for injection. ES cells to be injected were subcultured for 2 or 3 days before TE treatment, and then allowed to stand at 4° C. until microscopic manipulation.

As an injection pipette for ES cells, a Cook IVF polar body extrusion pipette (inner diameter: about 20 μm) was used. A pipette for holding the embryo was prepared by longitudinally enlarging a glass microtube with an outer diameter of 1 mm (NARISHIGE) using a microelectrode-generator (model P-98/IVF, Sutter), cutting the tube at a site with an outer diameter of 50 to 100 μm by using microforge (De Fonburun), and then reducing its bore size to 10 to 20 μm.

Each of the injection pipettes and holding pipettes has an about 5 mm-long tip bent about 30 degrees, and was connected to a micromanipulator (LEITZ). As a chamber for microscopic manipulation, a perforated glass slide was modified by attaching a cover slip thereto with beeswax. Two drops (about 20 $P_l$ each) of Hepes-buffered Whitten's medium supplemented with 0.3% BSA were placed on the slide and further over-layered with liquid paraffin (Nacalai Tesque 261-37 SP). About 100 ES cells were introduced into one drop, and 10 to 15 expanded blastocysts were introduced into the other drop. 10 to 15 ES cells were injected into each blastocyst.

All microscopic manipulations were performed with an inverted microscope. The manipulated embryos were cultured for 1 to 2 hours and then transferred into the uterine horns of 2-day pseudopregnant ICR recipient females. The recipient females giving no birth past their expected date of delivery were subjected to cesarean operation and their pups were brought up by foster mothers.

When Clone L236 ES cells were injected into 40 blastocysts from C57BL/6J mice, the injection succeeded in all 40 blastocysts (100% success). These 40 blastocysts were then transferred to the uterine horns of 2-day pseudopregnant ICR recipient females, thereby obtaining 5 pups. The coat color of regions originating from homologous recombinants is a color of wild-type, while the coat color of regions originating from C57BL/6J mice is black. All the resulting 5 pups were identified as chimeric mice based on their coat color and were morphologically males. Contribution (%) of the ES cells ranged from 10% to 90%, as determined by these chimeric mice's coat color. Likewise, chimeric mice were also produced from Clone L253 ES cells. Table 1 shows scores on the generation of these chimeric mice.

TABLE 1

Scores on generation of chimeric mice

| Clone No. | Injected/ manipulated embryos | Transferred embryos | Nidated embryos | Pups Total | (%) | ♂ | ♀ | Coat color chimeric pups Total | (%) | ♂ | ♀ | Contribution (%) of ES cells to coat color |
|---|---|---|---|---|---|---|---|---|---|---|---|---|
| L228 | 22/25 (88%) | 22 | 21 (95%) | 10 | 45 | 6 | 4 | 4 | 40 | 2 | 2 | ♂(70, 70) ♀(80, 5) |
| L236 | 40/40 (100%) | 40 | 24 (60%) | 14 | 35 | 11 | 3 | 5 | 36 | 5 | 0 | ♂(90, 90, 90, 70, 10) |
| L253 | 75/77 (97%) | 75 | 65 (87%) | 11 | 15 | 7 | 4 | 8 | 73 | 5 | 3 | ♂(95, 80, 70, 50, 30) ♀(60, 50, 10) |
| L44 | 64/72 (89%) | 64 | 42 (66%) | 16 | 25 | 16 | 0 | 11 | 69 | 11 | 0 | ♂(90, 90, 90, 60, 80, 70, 50, 40, 30, 20, 5) |

Example 4

Assay of Homologous Recombinants for Germline Transmission

The chimeric mice obtained in Example 3 were crossed with C57BL/6J mice to assay whether ES cell-derived pups were obtained. If the chimeric mice have germ cells derived from ES cells, the resulting pups have a wild-type coat color, whereas if they have germ cells derived from C57BL/6J mouse blastocysts, the resulting pups have a black coat color.

In the case of Clone L236 ES cells, all two male chimeric mice (No. L236-1 and -2), except for one mouse which died before sexual maturation, were found to give the germline transmission of ES cells. These two mice provided a ratio of pups of wild-type coat color to total pups of 32/44 and 19/44, respectively. In the case of Clone L254 ES cells, among 6 chimeric mice (No. L254-1 to -6), 4 mice (No. L254-1, -2, -4 and -5) were found to give the germline transmission of ES cells. These mice provided a ratio of pups of wild-type coat color to total pups of 4/15, 2/12, 2/14 and 4/9, respectively.

Next, a tail sample was taken from each pup of wild-type coat color for DNA extraction. The extracted DNA was PCR-assayed for transmission of the mutated α-TTP allele, thereby confirming that the mutated α-TTP allele was transmitted to both Clone L236 ES cell-derived pups and Clone L254 ES cell-derived pups.

Figure 3:
FIG. 3 shows the results of a PCR analysis using primers specific to the wild-type α-TTP gene and a mutated α-TTP gene, respectively.

Heterozygous deficient mice having a mutation on one allele of the α-TTP gene were crossed with each other to generate homozygous deficient mice having mutations on both alleles. PCR was employed for genotype analysis of wild-type, heterozygous deficient and homozygous deficient mice. More specifically, the presence of the mutated allele was detected by PCR using the above-mentioned primer set of ot-198 and PGK-1, while the presence of the wild-type allele was detected by PCR using a primer set of ot-198 and TTP N17 containing the sequence of Exon 1 (5' TCTCTG-CAATGCCCGCCGTGCTGTCCCG 3'; SEQ ID NO: 7). PCR using a primer set of ot-198 and TTP N17 was performed under the similar conditions as PCR using the above-mentioned primer set of ot-198 and PGK-1. The amplified products from PCR using these two primer sets were analyzed by electrophoresis. FIG. 3 shows the results obtained. Based on the electrophoresis analysis, a mouse having a detectable wild-type allele but no detectable mutated allele was identified as a wild-type mouse (Wi in FIG. 3); in contrast, a mouse having a detectable mutated allele but no detectable wild-type allele was identified as a homozygous deficient mouse (HO); and a mouse having both detectable wild-type and mutated alleles was identified as a heterozygous deficient mouse (HE).

Figures 1, 4:
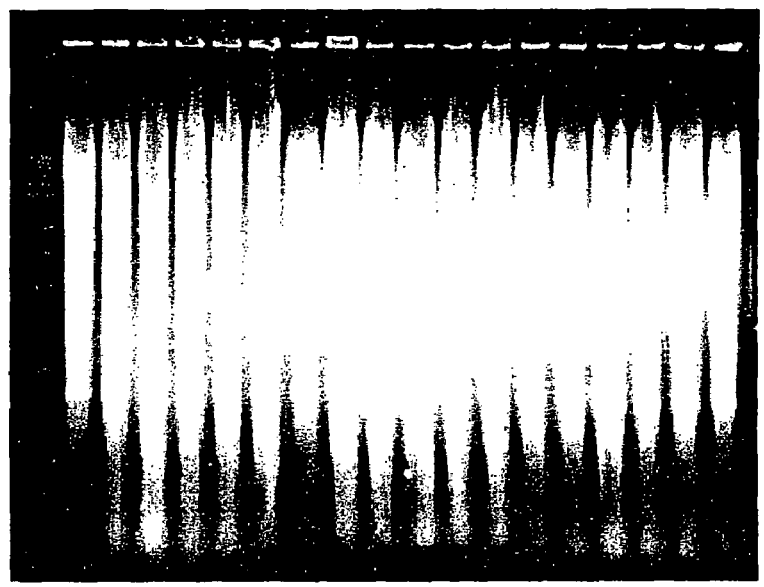
Figures 2, 4:
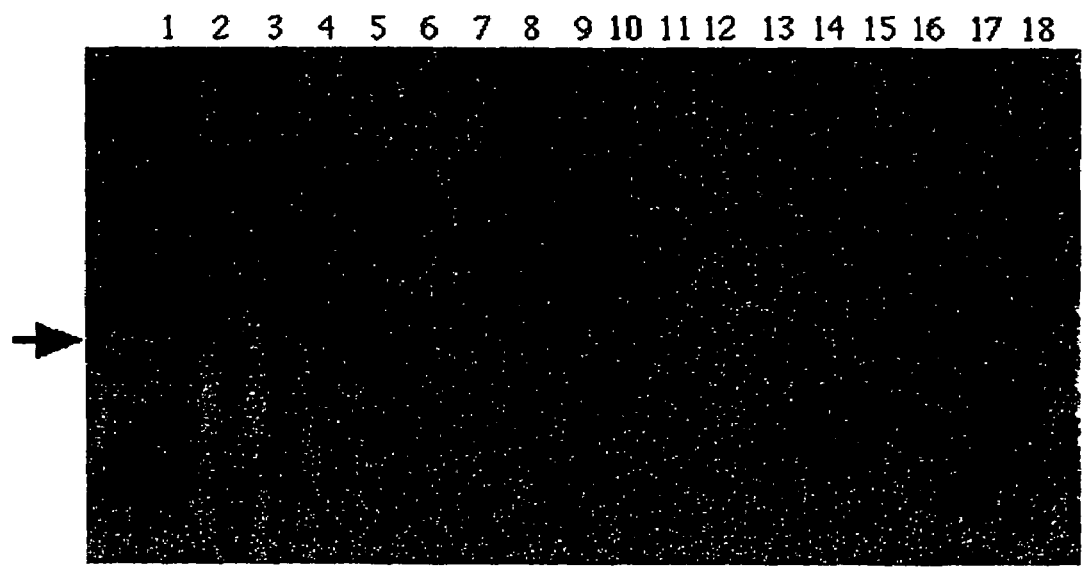

Genotype analysis was also performed by Southern hybridization. Mouse genomic DNA was cleaved with EcoRI and electrophoresed on a 0.7% agarose gel. 15 μg of genomic DNA was run in each lane. DNA in the gel was transferred to a Hybond N+nylon filter (Amersham), followed by Southern hybridization. As a probe, a sequence between SmaI-SmaI-SmaI sites around Exon 1 was used (see FIGS. 1 and 2). FIG. 4-1 shows the results of electrophoresis and FIG. 4-2 shows the results of Southern hybridization. As shown in FIG. 4-2, lanes 2, 3, 9, 12, 16 and 17 gave no detectable signal at a position indicated with an arrow (3.75 kbp). This suggests that mice corresponding to lanes 2, 3, 9, 12, 16 and 17 lack a sequence around Exon 1.

The above genotype analyses demonstrated that the ratio among wild-type, heterozygous deficient and homozygous deficient mice was 63:105:74 (total 242) and therefore substantially accorded with Mendel's law (1:2:1). In the case of 242 mice in total, a calculated ratio according to Mendel's law is 60.5:121:60.5.

Example 5

Analysis of α-TTP Expression in α-TTP-Deficient Mice

Total RNA and protein were collected from the liver of each mouse of 6 homozygous α-TTP-deficient mice, 5 heterozygous α-TTP-deficient mice and 4 wild-type mice, and confirmed for expression of α-TTP mRNA and protein by Northern blotting and Western blotting, respectively.

Figures 1, 5:
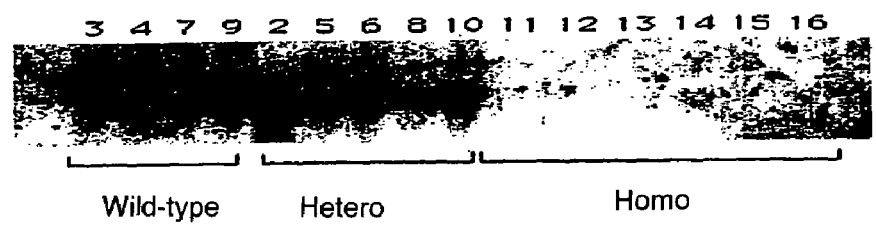
Figures 2, 5:
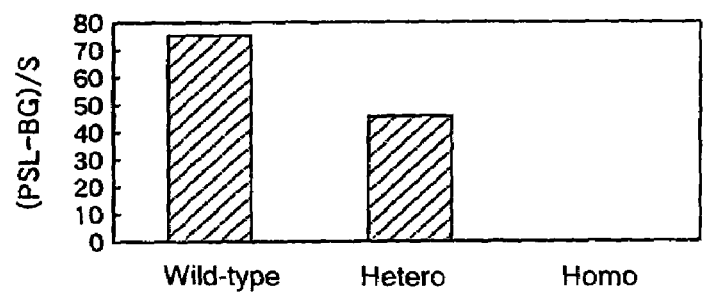

Northern blotting was performed on 10 μg of total RNA using the entire ORF of mouse α-TTP cDNA as a probe. FIG. 5-1 shows the results of Northern blotting. In addition, expression levels of α-TTP mRNA were determined from PSL values of a bioimage analyzer (BAS 5000, Fuji Film), and then compared among wild-type, heterozygous and homozygous mice. FIG. 5-2 shows the results obtained. As shown in this figure, the ratio of mRNA expression levels among wild-type, heterozygous and homozygous mice was 2:1:0.

Figure 6:
FIG. 6 shows the results of Western blotting using an anti-rat α-TTP polyclonal antibody.

Western blotting was performed using an anti-rat α-TTP polyclonal antibody and an alkaline phosphatase-conjugated anti-rabbit IgG as a secondary antibody. An AP conjugate substrate kit (Bio-Rad) was used to develop color. FIG. 6 shows the results of Western blotting. As shown in this figure, the ratio of protein expression levels among wild-type, heterozygous and homozygous mice was 2:1:0.

Figure 7:
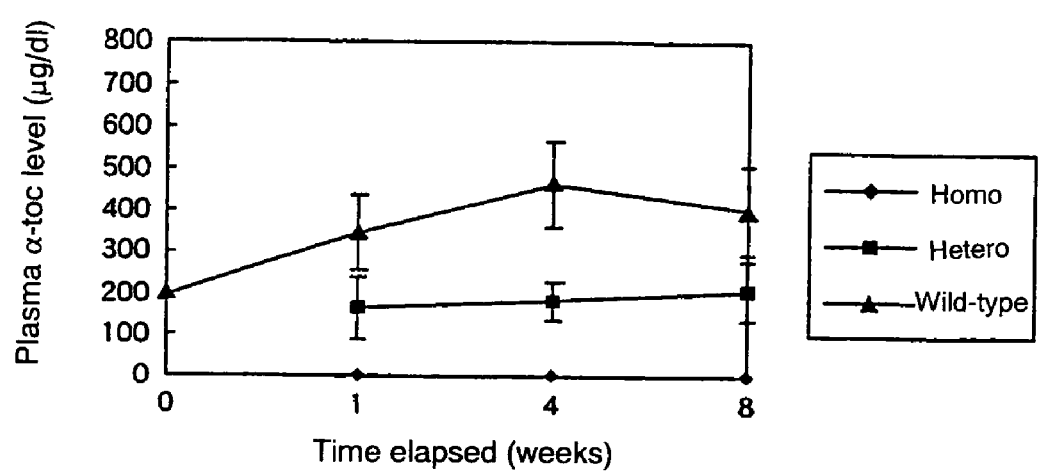
FIG. 7 shows a time course of blood tocopherol levels in mice.

Each of the homozygous α-TTP-deficient, heterozygous α-TTP-deficient and wild-type mice was fed with α-tocopherol at a concentration of 82 μmol/kg from 4 weeks of age. All mice were then assayed for their plasma α-tocopherol levels according to the method of Kim, H. S. et al. (Free Rad. Res. 28, 87–92, 1998). More specifically, 50 μl of mouse plasma collected using heparin was diluted with 950 $P_l$ of PBS, mixed with 1 ml of 6% pyrogarol in EtOH, and then allowed to stand at 70° C. for 2 minutes. After addition of 60% KOH (0.2 ml), the mixture was saponified at 70° C. for 30 minutes, vortexed with 5 ml of n-hexane and 2.5 ml of $H_2O$, and then centrifuged to collect the n-hexane layer (4 ml). The layer was evaporated and dissolved in 100 ml of ethanol, followed by HPLC analysis. HPLC was performed under the following conditions: column: IRIKA RP18 (250×4 mm), mobile phase: MeOH/$H_2$O/NaClO$_4$ (1000/2/7, v/v/w), detection: IRIKA Amperometric E-520 detector. Tocol was used as an internal standard. FIG. 7 shows the time course of α-tocopherol level in each mouse. As shown in FIG. 7, the homozygous deficient mice gave a plasma α-tocopherol level under the detection limit. The heterozygous deficient mice gave an about one-half plasma α-tocopherol level as compared with the wild-type mice. This suggested that the expression level of α-TTP was a factor in regulating blood α-tocopherol level.

Example 6

Fetal Resorption-Gestation Test

In view of the fact that vitamin E has been discovered as an anti-sterility agent, a fetal resorption-gestation test is widely used as a biological test for vitamin E deficiency (Biol. Syposia 12, 459, 1947). Namely, this test utilizes a phenomenon in which a pregnant animal fed with vitamin E-deficient diet does not maintain any further fetal development which leads to fetal resorption. This test was performed on the homozygous α-TTP-deficient mice to biologically confirm the state of vitamin E deficiency, thereby indicating that the homozygous α-TTP-deficient mice became pregnant, but showed fetal development stopped in the middle stage of pregnancy, and finally fetal resorption occurred (Table 2).

TABLE 2

Fetal resorption-gestation test in α-TTP knockout mice

| Genotype of female mouse | Mouse No. | x | Genotype of male mouse | Mouse No. | Nidated embyros | Regressed or resorbed fetuses | (%)* | Viable fetuses | (%)* |
|---|---|---|---|---|---|---|---|---|---|
| Homo | 42 | x | Homo | 15 | 16 | 16 | 100 | 0 | 0 |
|  | 44 | x |  | 17 | 16 | 16 | 100 | 0 | 0 |
|  | 46 | x |  | 31 | 7 | 7 | 100 | 0 | 0 |
|  | 27 | x |  | 4 | 0 | — |  | — |  |
|  | 6 | x |  | 3 | 0 | — |  |  |  |
|  | Total |  |  |  | 39 | 39 | 100 | 0 | 0 |
|  | 5 | x | Wild-type | C57BL/6J | 8 | 8 | 100 | 0 | 0 |
|  | 8 | x |  | C57BL/6J | 11 | 11 | 100 | 0 | 0 |
|  | 17 | x |  | C57BL/6J | 10 | 10 | 100 | 0 | 0 |
|  | 13 | x |  | C57BL/6J | 6 | 6 | 100 | 0 | 0 |
|  | Total |  |  |  | 35 | 35 | 100 | 0 | 0 |
| Wild-type | C57BL/6J | x | Homo | 10 | 4 | 1 | 25 | 3 | 75 |
|  | C57BL/6J | x |  | 2 | 9 | 2 | 22 | 7 | 78 |
|  | C57BL/6J | x |  | 12 | 9 | 0 | 0 | 9 | 100 |
|  | C57BL/6J | x |  | 15 | 9 | 9 | 100 | 0 | 0 |
|  | ICR | x |  | 15 | 15 | 0 | 0 | 15 | 100 |
|  | ICR | x |  | 15 | 16 | 2 | 13 | 14 | 87 |
|  | C57BL/6J | x |  | 31 | 10 | 10 | 100 | 0 | 0 |
|  | ICR | x |  | 31 | 16 | 1 | 6 | 15 | 94 |
|  | Total | x |  |  | 88 | 25 | 28 | 63 | 72 |

*% relative to nidated embryos

In turn, when wild-type 2-celled embryos were transferred to the uterine tubes of pseudopregnant homozygous deficient mice, the mice also showed fetal development stopped during pregnancy, and finally fetal resorption occurred (Table 3).

TABLE 3

Scores on fetal resorption-gestation test in α-TTP knockout homozygous females with transferred wild-type embryos

| Homozygous female No. | Genotype transferred embryo | Developmental stage of transferred embryo | Transferred embryos | Nidated embryos | (%)* | Regressed or resorbed fetuses | (%)** | Viable fetuses (18 days after transfer) | (%)** |
|---|---|---|---|---|---|---|---|---|---|
| 11 | Wild-type (ICR) | Pronucleus | 12 | 0 | 0 | — | — | — | — |
| 14 | Wild-type (ICR) | Pronucleus | 12 | 1 | 8% | 1 | 100% | 0 | 0% |
| 7 | Wild-type (ICR) | 2-celled | 12 | 11 | 92% | 11 | 100% | 0 | 0% |
| 15 | Wild-type (ICR) | 2-celled | 12 | 10 | 83% | 10 | 100% | 0 | 0% |
| Total |  |  | 48 | 22 | 46% | 22 | 100% | 0 | 0% |

*% relative to transferred embryos
**% relative to nidated embryos

These results demonstrated that vitamin E levels in pregnant females affected fetal development regardless of fetal genotype. Accordingly, the vitamin E deficient state in the homozygous α-TTP-deficient mice was supported by the biological test.

EFFECTS OF THE INVENTION

The present invention provides a mammal artificially modified to inhibit α-TTP gene expression. The mammal of the present invention is very useful as a tool for understanding mechanisms for the development of diseases caused by a disrupted α-TTP gene (e.g., familial isolated vitamin E deficiency) and disease conditions suspected to be associated with oxidative stress. It is also very useful as a tool for developing a therapeutic agent and/or method for these diseases.

What is claimed is:

1. A transgenic mouse whose genome comprises a homozygous disruption of the endogenous α-TTP gene, wherein α-TTP is not expressed and the transgenic mouse does not exhibit detectable plasma levels of α-tocopherol.

2. The transgenic mouse according to claim 1, wherein the mouse is a pregnant female, and wherein the pregnant female fails to maintain pregnancy as assayed by the fetal resorption-gestation test.

3. The transgenic mouse according to claim 1, wherein the disrupted endogenous α-TTP gene comprises an inserted marker gene.

4. A method for producing the transgenic mouse according to claim 1, comprising:
   (a) inserting a mouse embryonic stem cell into an embryo taken from a pregnant female to form a chimeric embryo, wherein the embryonic stem cell comprises a disrupted endogenous α-TTP gene;
   (b) transferring the chimeric embryo into the uterus of a female mouse;
   (c) allowing the embryo to undergo full fetal development to term to obtain a mouse comprising the disrupted endogenous α-TTP gene;
   (d) crossing a male mouse comprising the disrupted endogenous α-TTP gene with a female mouse comprising the disrupted endogenous α-TTP gene; and
   (e) screening the progeny obtained from the cross to identify the mouse according to claim 1.

5. A transgenic mouse whose genome comprises a heterozygous disruption of the endogenous α-TTP gene, wherein α-TTP is not expressed from the disrupted α-TTP allele and the transgenic mouse exhibits about one-half the plasma level of α-tocopherol of a corresponding mouse that does not comprise a disrupted endogenous α-TTP gene when the mice are fed with a diet comprising the same amount of α-tocopherol.

6. The transgenic mouse according to claim 5, wherein the disrupted endogenous α-TTP gene comprises an inserted marker gene.

7. A method for producing the transgenic mouse according to claim 5, comprising:
   (a) inserting a mouse embryonic stem cell into an embryo taken from a pregnant female to form a chimeric embryo, wherein the embryonic stem cell comprises a disrupted endogenous α-TTP gene;
   (b) transferring the chimeric embryo into the uterus of a female mouse;
   (c) allowing the embryo to undergo full fetal development to term to obtain a mouse comprising the disrupted endogenous α-TTP gene;
   (d) crossing a mouse comprising the disrupted endogenous α-TTP gene with a second mouse; and
   (e) screening the progeny obtained from the cross to identify the mouse according to claim 5.

\* \* \* \* \*

UNITED STATES PATENT AND TRADEMARK OFFICE
CERTIFICATE OF CORRECTION

PATENT NO. : 6,982,362 B1
DATED : January 3, 2006
INVENTOR(S) : Inoue et al.

It is certified that error appears in the above-identified patent and that said Letters Patent is hereby corrected as shown below:

<u>Title page,</u>
Item [54], Title, should read -- ANIMALS WITH KNOCKED OUT α-TOCOPHEROL TRANSFER PROTEIN GENE --.
Item [75], Inventors, "5-35-8-604 Koishikawa," should read -- 5-35-8-604, Koishikawa, --.
Item [73], Assignee, after "Arai" insert -- , Tokyo (JP) --.

Signed and Sealed this

Twenty-eighth Day of March, 2006

JON W. DUDAS
*Director of the United States Patent and Trademark Office*

SEQUENCE LISTING

<160> NUMBER OF SEQ ID NOS: 7

<210> SEQ ID NO 1
<211> LENGTH: 837
<212> TYPE: DNA
<213> ORGANISM: Mus musculus
<220> FEATURE:
<221> NAME/KEY: CDS
<222> LOCATION: (1)..(834)

<400> SEQUENCE: 1

```
atg gca gag atg cgg ccg ggg cca ttg gtt ggg aaa cag ctc aac gag      48
Met Ala Glu Met Arg Pro Gly Pro Leu Val Gly Lys Gln Leu Asn Glu
 1               5                  10                  15 ctg ccc gac cac tcg ccg ctg ctc cag ccc ggc ctg gcg gag ctc agg      96
Leu Pro Asp His Ser Pro Leu Leu Gln Pro Gly Leu Ala Glu Leu Arg
             20                  25                  30 cgc cgg gtg cag gag gca ggc gtc ccg cag acc ccg cag cct ctc aca     144
Arg Arg Val Gln Glu Ala Gly Val Pro Gln Thr Pro Gln Pro Leu Thr
         35                  40                  45 gac gct ttc ctg ctg cgc ttc ctg cgc gcc cgg gat ttc gat ctg gat     192
Asp Ala Phe Leu Leu Arg Phe Leu Arg Ala Arg Asp Phe Asp Leu Asp
     50                  55                  60 ctg gcc tgg cgc tta atg aaa aac tat tat aaa tgg cga gca gaa tgc     240
Leu Ala Trp Arg Leu Met Lys Asn Tyr Tyr Lys Trp Arg Ala Glu Cys
 65                  70                  75                  80 cca gaa tta agt gca gat cta cgc cct aga agt atc ctt gga ctt ctg     288
Pro Glu Leu Ser Ala Asp Leu Arg Pro Arg Ser Ile Leu Gly Leu Leu
                 85                  90                  95 aaa gct ggc tac cat ggc gtg ctc agg tcc cgg gat tct act ggc agt     336
Lys Ala Gly Tyr His Gly Val Leu Arg Ser Arg Asp Ser Thr Gly Ser
            100                 105                 110 aga gtt ctc att tac aga att gca tac tgg gac cca aaa gtt ttt aca     384
Arg Val Leu Ile Tyr Arg Ile Ala Tyr Trp Asp Pro Lys Val Phe Thr
        115                 120                 125 gct tat gat gta ttt cgt gta agt ctg atc aca tca gag ctc att gta     432
Ala Tyr Asp Val Phe Arg Val Ser Leu Ile Thr Ser Glu Leu Ile Val
    130                 135                 140 cag gag gtg gaa act caa cgc aat gga gtt aaa gct ata ttt gac ctg     480
Gln Glu Val Glu Thr Gln Arg Asn Gly Val Lys Ala Ile Phe Asp Leu
145                 150                 155                 160 gaa ggc tgg cag gtt tct cat gct ttc caa att acc cca tct gta gcc     528
Glu Gly Trp Gln Val Ser His Ala Phe Gln Ile Thr Pro Ser Val Ala
                165                 170                 175 aag aag att gct gct gta ctt aca gat tcc ttt cca ctg aaa gtt cgt     576
Lys Lys Ile Ala Ala Val Leu Thr Asp Ser Phe Pro Leu Lys Val Arg
            180                 185                 190 ggg atc cat ttg ata aat gag cca gtc att ttc cat gct gtc ttc tcc     624
Gly Ile His Leu Ile Asn Glu Pro Val Ile Phe His Ala Val Phe Ser
        195                 200                 205 atg att aaa cca ttt ctg act gaa aag att aag gac cgg att cat ctg     672
Met Ile Lys Pro Phe Leu Thr Glu Lys Ile Lys Asp Arg Ile His Leu
    210                 215                 220 cac ggg aac aac tac aaa tca agc atg ctt cag cac ttc cca gac att     720
His Gly Asn Asn Tyr Lys Ser Ser Met Leu Gln His Phe Pro Asp Ile
225                 230                 235                 240 ctt cct cgg gaa tat ggc ggt aaa gag ttc tcc atg gag gat att tgt     768
Leu Pro Arg Glu Tyr Gly Gly Lys Glu Phe Ser Met Glu Asp Ile Cys
                245                 250                 255
```

```
cag gag tgg aca aat ttt ata atg aag tct gaa gat tat ctc agc agc    816
Gln Glu Trp Thr Asn Phe Ile Met Lys Ser Glu Asp Tyr Leu Ser Ser
        260                 265                 270 att tct gag acc atc caa tga                                        837
Ile Ser Glu Thr Ile Gln
        275
```

<210> SEQ ID NO 2
<211> LENGTH: 278
<212> TYPE: PRT
<213> ORGANISM: Mus musculus

<400> SEQUENCE: 2

```
Met Ala Glu Met Arg Pro Gly Pro Leu Val Gly Lys Gln Leu Asn Glu
 1               5                  10                  15

Leu Pro Asp His Ser Pro Leu Leu Gln Pro Gly Leu Ala Glu Leu Arg
            20                  25                  30

Arg Arg Val Gln Glu Ala Gly Val Pro Gln Thr Pro Gln Pro Leu Thr
        35                  40                  45

Asp Ala Phe Leu Leu Arg Phe Leu Arg Ala Arg Asp Phe Asp Leu Asp
    50                  55                  60

Leu Ala Trp Arg Leu Met Lys Asn Tyr Tyr Lys Trp Arg Ala Glu Cys
65                  70                  75                  80

Pro Glu Leu Ser Ala Asp Leu Arg Pro Arg Ser Ile Leu Gly Leu Leu
                85                  90                  95

Lys Ala Gly Tyr His Gly Val Leu Arg Ser Arg Asp Ser Thr Gly Ser
            100                 105                 110

Arg Val Leu Ile Tyr Arg Ile Ala Tyr Trp Asp Pro Lys Val Phe Thr
        115                 120                 125

Ala Tyr Asp Val Phe Arg Val Ser Leu Ile Thr Ser Glu Leu Ile Val
    130                 135                 140

Gln Glu Val Glu Thr Gln Arg Asn Gly Val Lys Ala Ile Phe Asp Leu
145                 150                 155                 160

Glu Gly Trp Gln Val Ser His Ala Phe Gln Ile Thr Pro Ser Val Ala
                165                 170                 175

Lys Lys Ile Ala Ala Val Leu Thr Asp Ser Phe Pro Leu Lys Val Arg
            180                 185                 190

Gly Ile His Leu Ile Asn Glu Pro Val Ile Phe His Ala Val Phe Ser
        195                 200                 205

Met Ile Lys Pro Phe Leu Thr Glu Lys Ile Lys Asp Arg Ile His Leu
    210                 215                 220

His Gly Asn Asn Tyr Lys Ser Ser Met Leu Gln His Phe Pro Asp Ile
225                 230                 235                 240

Leu Pro Arg Glu Tyr Gly Gly Lys Glu Phe Ser Met Glu Asp Ile Cys
                245                 250                 255

Gln Glu Trp Thr Asn Phe Ile Met Lys Ser Glu Asp Tyr Leu Ser Ser
            260                 265                 270

Ile Ser Glu Thr Ile Gln
        275
```

<210> SEQ ID NO 3
<211> LENGTH: 2748
<212> TYPE: DNA
<213> ORGANISM: Mus musculus
<220> FEATURE:
<221> NAME/KEY: CDS
<222> LOCATION: (1139)..(1342)

-continued

```
<400> SEQUENCE: 3
gaattcaaag ctctcagccc ggtaaccaag cacccagcc agctctcttt gtgattcagg      60
ggttcacacc acaacacagc cgcttggcct tgttccctgg tgtttgctta atgttctcct    120
acaccatgga ggagatttac ctctgctcct tttacttcca gcccacacaa aaatgaaaaa    180
cgtctccaag gcaagagttc tgttttgagg atatcctcaa taatcggaac atggtctcta    240
cccaagagcc actccatcag acattcttgc tctgagttcc tttaaggcct ctttcactcg    300
caaaatcagt gttttgtgaa catgcactgc atattaagag gagttagttt tgtggacttt    360
cttctgttca ggtggcagtt caagtgtagg ataattttaa tggaaatgaa ggaaaaatac    420
ttccgtgtgt tcattcagat ttcgcggtca tctctgtgta ttcttcagca gacatccttc    480
aggttcctta gtaagggttt tgattgaga gactggtggc atctaaacac atacatcgtt    540
agtgtttaaa aatgtgacct ccccaccccg ctctcctttc tctagtagag ccagatgcca    600
agatctggaa gcattttcct ggagagaagc aaggaggagg aggaggagac tgccaaaagg    660
tgacttcctt gagttacatt ttggaaacta gttagaatgc cagagatggc ctgagctcag    720
ccttaaggaa ggggtcagga ggaggggttcc tgagtgtctg ctacccaagc taattaaaga    780
gccgtttaca gtgttccctg attccaaaac ggacagaggg ggaagggcaa cgaggaaagg    840
gtgagaaaag tctctggcag cctgattata aacatcccaa gtaacttttc gacttcccgt    900
tctttaggtt caacactagt gactttccct tccctggga ctggctgcgg ttaccctggt    960
gagcaccgga gggcaccacg tgggcttctt taagagggcg ccgtgaccct tgcaccggcg   1020
gggcacggga gatcggggcg gcccgggtga gtgtgcgtgg ggcggcgtcc acggcggggg   1080
gcggagggtg gctctgggcc cgcacttttc cccctgtcgc cgggacagca cggcgggc     1138 atg gca gag atg cgg ccg ggg cca ttg gtt ggg aaa cag ctc aac gag    1186
Met Ala Glu Met Arg Pro Gly Pro Leu Val Gly Lys Gln Leu Asn Glu
  1               5                  10                  15 ctg ccc gac cac tcg ccg ctc ctc cag ccc ggc ctg gct gag ctc agg    1234
Leu Pro Asp His Ser Pro Leu Leu Gln Pro Gly Leu Ala Glu Leu Arg
              20                  25                  30 cgc cgg gtg cag gag gca ggc gtc ccg cag acc ccg cag cct ctc aca    1282
Arg Arg Val Gln Glu Ala Gly Val Pro Gln Thr Pro Gln Pro Leu Thr
          35                  40                  45 gac gct ttc ctg ctg cgc ttc ctg cgc gcc cgg gat ttc gat ctg gat    1330
Asp Ala Phe Leu Leu Arg Phe Leu Arg Ala Arg Asp Phe Asp Leu Asp
      50                  55                  60 ctg gcc tgg cgc gtaagtgtgc accgggggcg ggcagagctc ggcgacggcg        1382
Leu Ala Trp Arg
 65 gaatccacgc gcgccgagcg tggcagtgtg actgcaggcg cgcccagaac cccgatttcg   1442 cccccgccga tgttttggtc cccgccgccg cgaggacatc ccgtggacta ctagggtcct   1502 tgggaattaa acaaagtgga gatccctgtc ccccggggtg ctcagctgtg ttaactgaat   1562 agataactag gtgtggacag aggacgacga aatggacatc taaaggcatc ttgaaaaga    1622 ctatgttaat agagctaaat gcacagtttg gcatgtttga macccagggc agtacagatg   1682 atttctttta tgtttcaggt attcacaaca cactggcctt ggggcaagag agatggggcc   1742 ttagggtcag ggagatgcga ccttgacttt gtccctcttg gggtcagcac ccttatctgt   1802 tcagtaactg tgaggacatg acagtagttt cgagaattgc acattaacct ggaatgctag   1862 aacaagatgt gccaaaccct gtgcttggca cggagaaagt agtcagtgat cagcaggctg   1922 cggatttcca acatgcccctg ggtttatgaa acttttttta ttggataagc accaagtatg   1982
```

-continued

```
gcaaaaaaca ccacaaacaa tacaaaacag gaaaaacdtc aaaggaattt cctaaaagaa    2042
aagaatttcc caacacaaac tctagttaga ccttgaggac ccagaagtat ggcattacct    2102
gttacgtcaa gcctgtgtaa caatgtcacg caaacatgcg ctgtgagttt attttccttt    2162
tgcaaatctc aactgcatgc tgttatagaa tcaggtcatg tgaacatgtg ctcacaccta    2222
ctactctttt gggaatatct agtcagtttt ttgtttgtgg ctgtagagat tgttaccggg    2282
cgggtgctgt taggccctat gctgatcgtt catccctaca ttcagtgatg ggggacccag    2342
cgctgccatg ttcactgttc atctcttcat ttcatttgga gtttctcctt cttttttcttt    2402 cttttcttt tcttttcttt ttaatatcca cacactgcct agcagtatac aaatgccatc    2462
aacaggtgag tattttcttc ctcccctgac tgcatctaag ttggtctttg tctgtacaca    2522
taaattggaa catatcctta ttgaacaaat ccatcagttg ctgaagcacg acgcagacat    2582
gtttactgtt gaggagcgca ccacctttgc agggagtttt cagtgtttgc tactctgatg    2642
aaatgcacac tgcatagtga cgtcttttt tctctattgt tatgtacact gtcttaccaa    2702
atrggatgta tgcctgctag atgaggatag ttttgcattt cattat                   2748
```

<210> SEQ ID NO 4
<211> LENGTH: 68
<212> TYPE: PRT
<213> ORGANISM: Mus musculus

<400> SEQUENCE: 4

```
Met Ala Glu Met Arg Pro Gly Pro Leu Val Gly Lys Gln Leu Asn Glu
 1               5                  10                  15

Leu Pro Asp His Ser Pro Leu Leu Gln Pro Gly Leu Ala Glu Leu Arg
            20                  25                  30

Arg Arg Val Gln Glu Ala Gly Val Pro Gln Thr Pro Gln Pro Leu Thr
        35                  40                  45

Asp Ala Phe Leu Leu Arg Phe Leu Arg Ala Arg Asp Phe Asp Leu Asp
    50                  55                  60

Leu Ala Trp Arg
 65
```

<210> SEQ ID NO 5
<211> LENGTH: 28
<212> TYPE: DNA
<213> ORGANISM: Artificial Sequence
<220> FEATURE:
<223> OTHER INFORMATION: :

<400> SEQUENCE: 5
gctaaagcgc atgctccaga ctgccttg                                         28

<210> SEQ ID NO 6
<211> LENGTH: 31
<212> TYPE: DNA
<213> ORGANISM: Artificial Sequence
<220> FEATURE:
<223> OTHER INFORMATION: :

<400> SEQUENCE: 6
agcccacaca aaatgaaaaa acgtctccaa g                                     31

<210> SEQ ID NO 7
<211> LENGTH: 28
<212> TYPE: DNA
<213> ORGANISM: Artificial Sequence

```
<220> FEATURE:
<223> OTHER INFORMATION: :

<400> SEQUENCE: 7
tctctgcaat gcccgccgtg ctgtcccg                                              28

<210> SEQ ID NO 8
<211> LENGTH: 22
<212> TYPE: DNA
<213> ORGANISM: Artificial Sequence
<220> FEATURE:
<223> OTHER INFORMATION: :

<400> SEQUENCE: 8
aggaattcat ggcagagatg cg                                                    22

<210> SEQ ID NO 9
<211> LENGTH: 22
<212> TYPE: DNA
<213> ORGANISM: Artificial Sequence
<220> FEATURE:
<223> OTHER INFORMATION: :

<400> SEQUENCE: 9
agggcgtaga tctgcactta at                                                    22
```